(12) United States Patent
Frenkel et al.

(10) Patent No.: US 8,320,992 B2
(45) Date of Patent: Nov. 27, 2012

(54) METHOD AND SYSTEM FOR SUPERIMPOSING THREE DIMENSIONAL MEDICAL INFORMATION ON A THREE DIMENSIONAL IMAGE

(75) Inventors: Tami Frenkel, Savyon (IL); Avi Yaron, Tenafly, NJ (US)

(73) Assignee: Visionsense Ltd., Petah Tikva (IL)

( * ) Notice: Subject to any disclaimer, the term of this patent is extended or adjusted under 35 U.S.C. 154(b) by 1091 days.

(21) Appl. No.: 11/866,828

(22) Filed: Oct. 3, 2007

(65) Prior Publication Data
US 2008/0119728 A1 May 22, 2008

Related U.S. Application Data

(60) Provisional application No. 60/849,575, filed on Oct. 5, 2006.

(51) Int. Cl.
*A61B 5/05* (2006.01)
(52) U.S. Cl. ......... 600/424; 600/426; 600/427; 600/407
(58) Field of Classification Search .................. 600/424, 600/426, 427
See application file for complete search history.

(56) References Cited

U.S. PATENT DOCUMENTS

| | | | |
|---|---|---|---|
| 5,595,193 A * | 1/1997 | Walus et al. .................. | 128/898 |
| 6,640,127 B1 | 10/2003 | Kosaka et al. | |
| 6,741,883 B2 | 5/2004 | Gildenberg | |
| 6,782,287 B2 | 8/2004 | Grzeszczuk et al. | |
| 6,856,827 B2 | 2/2005 | Seeley et al. | |
| 2002/0077543 A1* | 6/2002 | Grzeszczuk et al. .......... | 600/424 |
| 2004/0122311 A1* | 6/2004 | Cosman ....................... | 600/427 |

* cited by examiner

*Primary Examiner* — Brian Casler
*Assistant Examiner* — Joel Lamprecht
(74) *Attorney, Agent, or Firm* — Merchant & Gould P.C.

(57) ABSTRACT

A system for video based registration between images during a skeletal medical procedure includes a stereoscopic camera, a two dimensional image detector and a registration processor. The camera is associated with a stereoscopic coordinate system, the camera acquires a stereoscopic image pair of fiducial marks fixed onto a skeletal structure. Fiducial representations of the fiducial marks appear on the stereoscopic image pair, and a skeletal representation of the skeletal structure appears on two different 2D images. The registration processor registers a stereoscopic coordinate system with a 3D coordinate system associated with a volumetric image detector, and superimposes 3D information on at least one volumetric image. The registration processor registers the stereoscopic coordinate system with the 3D coordinate system by registering the stereoscopic coordinate system with the 2D coordinate system and by registering the 2D coordinate system with the 3D coordinate system.

25 Claims, 10 Drawing Sheets

METHOD AND SYSTEM FOR SUPERIMPOSING THREE DIMENSIONAL MEDICAL INFORMATION ON A THREE DIMENSIONAL IMAGE

FIELD OF THE DISCLOSED TECHNIQUE

The disclosed technique relates to surgery of skeletal or joints structures (e.g., such as spine, knee & hip, shoulder, ankle, elbow) or skull and neurosurgery in general, and to methods and system for superimposing two or three dimensional medical information on a three dimensional or stereoscopic image, in particular.

BACKGROUND OF THE DISCLOSED TECHNIQUE

During surgery procedures, especially in spine procedures, medical staff is required to determine the position orientation and the path of medical devices (e.g., pedicle screws, rods, joints & other implants) and surgical tools (e.g., screwdriver, drill, surgical knife) to avoid damage to the spinal cord, aorta or other relevant organs. Furthermore, the physician may be required to determine additional medical information such as the dimensions of a resected disc (i.e., to determine if the entire disc was resected) or the dimensions of a cavity size (e.g., to determined the size of an implant). During these surgery procedures, the medical staff acquires the position orientation and the path of medical devices or that additional medical information utilizing a fluoroscopic imaging system to image the anatomy and the medical devices in the surgical area. Thus, the medical staff, and the patient are exposed to radiation doses due to the use of the fluoroscopic imaging system.

U.S. Pat. No. 6,741,883 issued to Gildenberg et al, and entitled "Audible Feedback from Positional Guidance Systems", is directed to a system for generating audible feedback to assist with the precise insertion of a pedicle screw. The feedback generating system includes a computer system, one visualizing video camera, two localizing video cameras, eight fiducial markers, a medical probe and a loudspeaker. The computer system includes a processor and a monitor. The computer is coupled with all the cameras and with the loudspeaker. The computer stores a reconstructed three-dimensional (3D) volumetric image of the relevant part of the body of the patient. Four fiducial markers are mounted on the body of the patient in the proximity to the surgical region (e.g., in brain surgery the fiducial markers are on the top of the head, the back head, the temporal area and the nose bridge). Four more fiducial markers are mounted on the medical probe allowing the tracking of the position and orientation of the medical probe.

The 3D volumetric image is reconstructed before the surgery from volumetric images taken by computerized tomography scan or magnetic resonance imaging scan. The three cameras acquire images of the medical probe and the surgical field, and send the image data to the computer. The computer generates a three dimensional image from the image data obtained by the cameras. The computer superimposes a representation of the location and position of the probe, obtained by the camera images, on the 3D image generated by the computer. The computer coordinates and matches the superimposed three dimensional image with the three dimensional volumetric image, using the fiducial markers on the patient and on the medical probe. The monitor displays the combined image. The computer sends the loudspeaker signals corresponding to the location of the probe relative to the body of the patient. The loudspeaker generates an audio signal to augment the visual display on the monitor to help a surgeon in navigating the probe.

U.S. Pat. No. 6,856,827 issued to Seeley et al., and entitled "Fluoroscopic Tracking and Visualization System", is directed to a system for surgical imaging. The visualization system includes a fluoroscope, a processor, a display and a plurality of tracking elements. The processor is coupled with the fluoroscope and with the display. The first tracking element is mounted on the medical probe. The second tracking element is mounted on the fluoroscope. The third tracking element is mounted on the body of a patient. Thus so the fluoroscope, the patient and the probe are dynamically referenced.

The fluoroscope acquires images of the body of the patient from several angles. The processor constructs a three dimensional image of the body of the patient, that is dynamically referenced to the medical probe and the patient, from the fluoroscope images. The processor fuses the three dimensional image with a preoperative volumetric data for simultaneous display of both sets of images. The preoperative volumetric data is a volumetric data acquired prior to the medical procedure by a volumetric imager (e.g., CT, PET or MRI).

U.S. Pat. No. 6,782,287 B2 issued to Grzeszczuk et al. and entitled "Method and Apparatus for Tracking a Medical Instrument Based on Image Registration" is directed to a method, a system and apparatus for tracking a surgical instrument with respect to the patient's anatomy and pre-operative diagnostic scans, using intra-operative fluoroscopy and to provide stereoscopic registration in order to relate the patient's anatomy to the pre-operative diagnostic scans in 3-D. The system includes a fluoroscopic device, a surgical instrument, a position sensor and a computer system. The fluoroscopic device includes an X-ray camera and an image intensifier. The surgical instrument and image intensifier each include emitters, (such as LEDs). The position sensor is coupled to the computer system, and the computer system is coupled to the X-ray camera.

The position sensor tracks the position of the emitters, and supplies the computer system with data required to perform transformations between various coordinate systems. The images acquired by the X-ray camera are also supplied to the computer system for processing. These images are used to register a pre-operative CT data set to the patient's reference frame. These images then are used to compute the C-Arm-to-CT data set registration. The tracking of the surgical tool involves the back-projection of the surgical tool onto the reference frame of the CT data set using stereoscopic techniques, by utilizing at least two fluoroscopic views of the surgical tool. Using this composite rendition, the surgical tool is then tracked with respect to a 3-D model of the anatomical structure of interest.

U.S. Pat. No. 6,640,127 to Kosaka et al, entitled "Surgical Operation Navigating System Using a Reference Frame", directs to a surgical operation navigating system using such a reference frame. The system includes a reference frame fitted with fiducial markers, an imaging unit (e.g., CT or MRI), a surgical instrument of an observation unit for observing the site of operation, a position sensor for detecting the attitude of the surgical instrument or the observation unit and a display, all coupled with a computer. The computer registers the coordinate systems of the position sensor, the surgical instrument of an observation unit and the images acquired by the imaging unit. The display displays navigation related information and image information provided by the computer.

SUMMARY OF THE PRESENT DISCLOSED TECHNIQUE

It is an object of the disclosed technique to provide a novel method and system for performing video based registration between images during a skeletal medical procedure.

In accordance with the disclosed technique, there is thus provided a system for video based registration between images during a skeletal medical procedure. The system includes a stereoscopic camera, a two dimensional (2D) image detector and a registration processor. The registration processor is coupled with the stereoscopic camera and with the (2D) image detector. The stereoscopic camera is associated with a stereoscopic coordinate system and acquires a stereoscopic image pair of a fiducial mark the fiducial mark being fixed onto a skeletal structure, a first fiducial representation of the fiducial mark being apparent on the stereoscopic image pair. The 2D image detector is associated with a 2D coordinate system, and acquires at least two substantially different 2D images of the skeletal structure a second fiducial representation of the fiducial mark and a first skeletal representation the skeletal structure is apparent on the two perpendicular images. The registration processor, registers the stereoscopic coordinate system with a 3D coordinate system associated with a volumetric image detector, and superimposes 3D information on at least one volumetric image acquired by the volumetric image detector, according to the registration. The registration processor registers the stereoscopic coordinate system with the 3D coordinate system by registering the stereoscopic coordinate system with the 2D coordinate system and by registering the 2D coordinate system with the 3D coordinate system. The registration processor registers the stereoscopic coordinate system using the first fiducial representation apparent in the stereoscopic image pair, and using the second fiducial representation apparent in the at least two substantially different 2D images. The registration processor registers the 2D coordinate system with the 3D coordinate system using the first skeletal representation, apparent in the at least two substantially different 2D images, and the second skeletal representation apparent in the at least one volumetric image.

In accordance with another aspect of the disclosed technique, there is thus provided a method for video based registration between images during a skeletal medical procedure, the method comprising the procedures of pre-acquiring a volumetric image of the skeletal structure, the at least one volumetric image is associated with a three dimensional (3D) coordinate system, fixing a fiducial mark onto the skeletal structure, acquiring a stereoscopic image pair, the stereoscopic image pair, a first fiducial representation of the fiducial mark is apparent on the stereoscopic image pair, the stereoscopic image pair is associated with a stereoscopic coordinate system. The method further includes the procedure of acquiring at least two substantially different two dimensional (2D) images, a second fiducial representation of the fiducial mark, and a first skeletal representation of the skeletal structure, both is apparent on the at least two 2D images, the at least two 2D images is associated with a 2D coordinate system, registering the stereoscopic coordinate system with the 2D coordinate system using the first fiducial representation apparent in the stereoscopic image pair, and the second fiducial representation apparent in the at least two substantially different 2D images, registering the 2D coordinate system with the 3D coordinate system using the first skeletal representation apparent in the at least two substantially different 2D images, and a second skeletal representation of the skeletal structure, the second skeletal representation is included in the at least one volumetric image, and, registering the stereoscopic coordinate system with the 3D coordinate system, according to the registrations between the stereoscopic coordinate system and the 2D coordinate system and according to the registration between the 2D coordinate system and the 3D coordinate system;

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1:
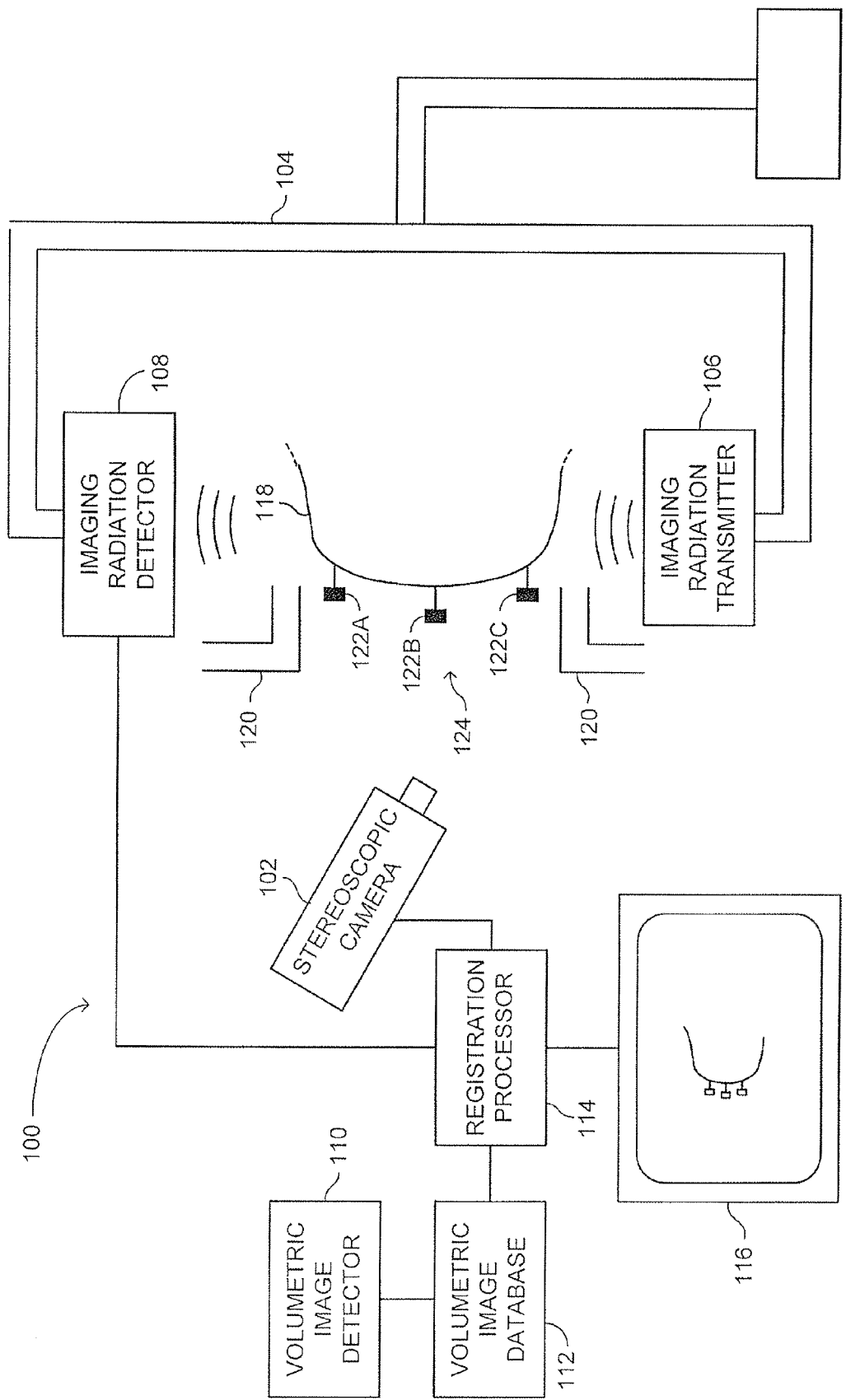
FIG. 1 is a schematic illustration of a system for performing video based registration between images, during a spinal medical surgery procedure, constructed and operative in accordance with an embodiment of the disclosed technique.

The disclosed technique overcomes the disadvantages of the prior art by providing a system and a method for performing video based registration between images. Consequent of this registration, two dimensional (2D) or three dimensional (3D) guidance or medical information can be superimposed a volumetric image of a skeletal structure or joints structures (e.g., the spinal bone, the knee, the hip or the elbow or skull). The three dimensional information is acquired by a stereoscopic camera.

The system according to the disclosed technique, acquires a volumetric image (e.g., either pre-operative or intra-operative CT, MRI, PET, Ultra-Sound), associated with a three dimensional coordinate system (i.e., a relative coordinate system is defined for the image and each point in the image space is defined by a coordinate vector within that coordinate system), of the volume of interest. A representation of the skeletal or joints structures (e.g., a vertebra, knee, hip, shoulder, elbow, and skull) is apparent in the volumetric acquired image (i.e., either 2D or reconstructed 3D). A stereoscopic camera, associated with another 3D coordinate system, acquires a stereoscopic image pair of the 3D surface. A representation of a fiducial mark, fixed onto that skeletal structure, is apparent in the stereoscopic image pair. A 2D image detector (e.g., an X-ray image detector or an Ultrasound image detector), associated with a 2D coordinate system, acquires at least two 2D images of the volume of interest from substantially different angles. A representation of the fiducial mark and a representation of the skeletal or joints structures represented in the volumetric image are apparent in the two 2D images. A registration processor registers the 3D coordinate system associated with the stereoscopic image pair with the 3D coordinate system associated with the volumetric image. Thus, the system provides the user with real time 3D information. This 3D information may be image guidance information such as position and orientation validation of medical devices (e.g., pedicle screws, rods, joints & other implants) or the surgical tools (e.g., screwdriver, drill, surgical knife). The 3D information may further be medical information such as the dimensions of a resected disc or the dimensions of a cavity, combined with video images, all in real-time during the surgical procedure. It is noted that the term "image" herein refers to the values of image elements (i.e., pixels) values stored in a memory after the acquired values were corrected for distortions and aberrations.

The 3D coordinate system associated with the volumetric image will be referred to hereinafter as "3D coordinate system". The 3D coordinate system associated with the stereoscopic image pair will be referred to hereinafter as "stereoscopic coordinate system". The 2D coordinate system associated with the two 2D images will be referred to hereinafter as "2D coordinate system". The term "registration" refers to finding a transformation associating the coordinates of each point in one coordinate system to the coordinates of the same points in another coordinate system.

A volumetric image of a treated area provides the user with valuable visual information (e.g., the position of the spine and the position of a spinal bone). A stereoscopic image pair, acquired by a stereoscopic camera, provides the user with stereoscopic visualization of the same treated area. Furthermore, 3D guidance and medical information can be determined from this stereoscopic image pair. 3D guidance information is, for example, the 3D position and orientation of a medical device intended to treat a skeletal structure. 3D medical information is, for example, or size of tissues (e.g., tumors, pedicle, vertebra, spinous process, transverse process) or cavities in the treated area (e.g., resected disk, resected nucleus). Thus, in the medical device case, superimposing a representation of the medical device on the volumetric image provides the user, for example, with information regarding the position of the medical device relative to the spine and to the spinal bone. Furthermore, the projection of the path of the medical device may also be superimposed on the volumetric image. To superimpose medical information, obtained by a stereoscopic camera, on a volumetric image, it is required to register the stereoscopic coordinate system with the 3D coordinate system.

Reference is now made to FIG. 1, which is a schematic illustration of a system, generally referenced 100, for performing video based registration between images, during a spinal medical surgery procedure, constructed and operative in accordance with an embodiment of the disclosed technique. System 100 includes a stereoscopic camera 102, a 2D imaging system 104, a volumetric image detector 110 and volumetric image database 112, a registration processor 114 and a display 116. Imaging system 104 includes an imaging radiation transmitter 106 and an imaging radiation detector 108.

Registration processor 114 is coupled with stereoscopic camera 102, with imaging system 104, with volumetric image database 112 and with display 116. Volumetric image database 112 is further coupled with volumetric image detector 110.

Prior to the medical procedure, volumetric image detector 110 acquires a volumetric image (e.g., CT, MRI, PET) of the area of a spinal bone of interest such as spinal bone 118 and stores this volumetric image in volumetric image database 112. A representation of spinal bone 118 is apparent in the volumetric image (not shown). The volumetric image is associated with a 3D coordinate system.

During the spinal medical procedure, the user exposes spinal bone 118 with retractor 120. After retractor 120 is in place, the user fixes fiducial mark 124 to bone 118. Fiducial mark 124 includes three fiducial points 122A, 122B and 122C, each independently fixed onto bone 118. The user may fix fiducial mark 124 to one or both of the transverse processes or to the spinous process. Types of fiducial marks will be further explained in conjunction with FIGS. 7A, 7B, 8, 9A, 9B, 9C, 9D, and 9E.

After the user fixes fiducial mark 124 onto spinal bone 118, 2D imaging system 104 acquires two 2D images from substantially different angles. A representation of spinal bone 118 and a representation of fiducial mark 124 are apparent in these 2D images. The 2D images are associated with a 2D coordinate system.

Stereoscopic camera 102 acquires a stereoscopic image pair. A representation of fiducial mark 124 is apparent in this stereoscopic image pair. The stereoscopic image pair is associated with a stereoscopic coordinate system.

Registration processor 114 registers stereoscopic coordinate system with 3D coordinate system. Registration processor 114 achieves this registration by registering the stereoscopic coordinate system with the 2D coordinate system and registering the 2D coordinate system with the 3D coordinate system.

Registration processor 114 registers the stereoscopic coordinate system with the 2D coordinate system using the representations of fiducial mark 124 in the stereoscopic image pair and in the two 2D images. Registration processor 114 registers the 2D coordinate system with the 3D coordinate system using the representations of the spinal bone in the two 2D images and in the volumetric image. As a result to the registration between the stereoscopic coordinate system and the 3D coordinate system, registration processor 114 may superimpose 3D guidance information or 3D medical information, determined from the stereoscopic image pair on the 3D volumetric image. Alternatively, registration processor 114 may superimpose 3D medical information acquired by volumetric image detector on the stereoscopic image pair. Display 116 displays 2D or 3D medical and guidance information, acquired by the stereoscopic camera, superimposed on the volumetric image.

Alternatively, display 116 displays 3D medical and guidance information, acquired by the stereoscopic camera, superimposed on a stereoscopic image pair. The user controls via registration process 114 the transparency of the 3D medical information and the volumetric image, to present and enhance the needed image and information (e.g., can vary between at any level between oblique to invisible). It is noted that when display 116 displays 3D guidance information (e.g., a representation of the position and orientation of a screwdriver) on the volumetric image, the image content (e.g., a representation of vertebra) may move relative to this guidance information.

Consequent to superimposing 3D guidance information or 3D medical information on the volumetric image, the user can view this 3D information with minimal use of fluoroscopic imaging system. It is noted that registration processor 114 registers the 3D coordinate system with the stereoscopic coordinate system for each stereoscopic image pair stereoscopic camera 102 acquires. Registration processor 114 may adjust the registration, according to the changes apparent in the last acquired stereoscopic, relative to any one of the previously acquired stereoscopic image pairs. When the registration between the stereoscopic coordinate system and the 3D coordinate system is lost (e.g., when fiducial mark 124 is not in the field of view of stereoscopic camera 102), the image displayed on display 116 will be held still until registration processor 114 re-registers the stereoscopic coordinate system with the 3D coordinate system.

In accordance with another embodiment of the disclosed technique, a navigation sensor (not shown in FIG. 1) is fitted on stereoscopic camera 102. The navigation sensor is coupled with a navigation system (also not shown in FIG. 1) and the navigation system (e.g., optical navigation system or electromagnetic navigation system) is coupled with registration processor 114. Registration processor 114 registers the coordinate system associated with the navigation system with the stereoscopic coordinate system. For example, registration processor 114 registers the position of the navigation sensor, fitted on stereoscopic camera 102, in the navigation system coordinate system with the stereoscopic coordinate system. Consequently, since registration processor 114 registered the stereoscopic coordinate system with the 2D coordinate system and with the 3D coordinate system, the coordinate system associated with the navigation system is also registered with the 2D coordinate system and with the 3D coordinate system. Thus, navigation system tracks the position of the camera and consequently, a representation of the camera may be superimposed on the volumetric image or on the 2D image. Furthermore, the stereoscopic camera may be used to measure distances to known objects, thus improve the accuracy of the navigation system.

It is noted that although FIG. 1 depicts a spinal surgical procedure employing a retractor, the disclosed technique is not limited thereto. Retractor 120 may be replaced with a cannula. Further more, the disclosed technique is also compatible with open surgery procedures and Minimal Invasive Surgery (MIS) or Least Invasive Surgery (LIS) procedures not employing a cannula or a retractor, or percutaneous procedures of any skeletal or joints structures. It is further noted that although FIG. 1 depicts fiducial mark 124 fixed onto a spinal bone, fiducial marks may be fixed onto other locations (e.g., onto the skull during neurological surgery) or even onto different surgical devices (e.g., onto the screw or the screwdriver).

In Accordance with a further embodiment of the disclosed technique, several stereoscopic cameras may be used during the surgical procedure. For example, an operational stereoscopic camera may observe only the area the user treats, or may be fixed onto a pedicle screw or a screwdriver or drill, thus providing the user with information regarding the position and orientation of the pedicle screw. However, the fiducial mark used for registration, may not be in the field of view of this operational stereoscopic camera. Therefore, a reference stereoscopic camera observes the entire surgical site, or parts thereof, including the fiducial mark. The user can operate these stereoscopic cameras simultaneously, successively or only when needed (e.g., for registration purposes, navigation purposes, information gathering or viewing purposes).

Figure 2:
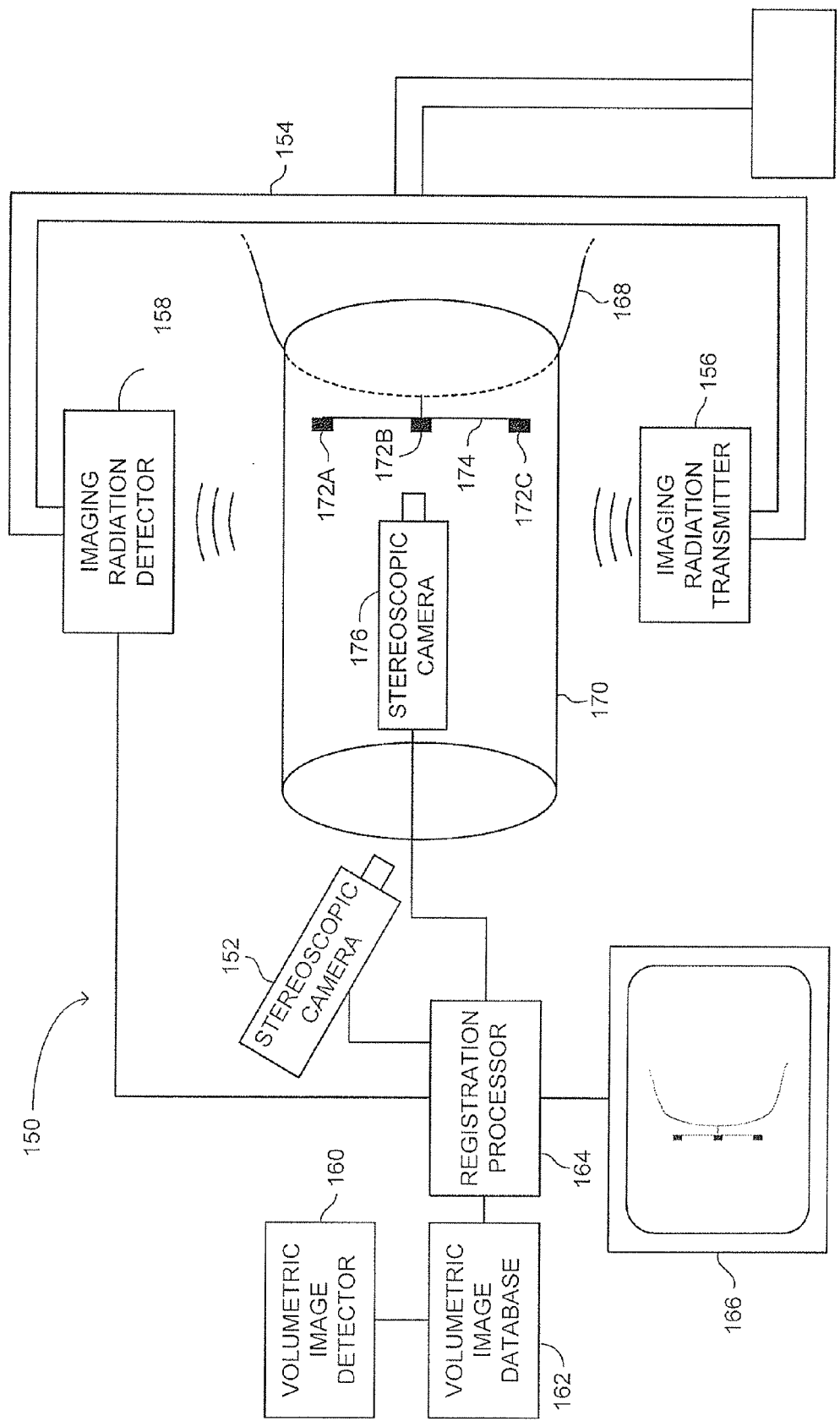
FIG. 2 is a schematic illustration of a system for performing video based registration between images, during a spinal medical surgery procedure, constructed and operative in accordance with another embodiment of the disclosed technique.

Reference is now made to FIG. 2, which is a schematic illustration of a system, generally referenced 150, for performing video based registration between images, during a spinal medical surgery procedure, constructed and operative in accordance with another embodiment of the disclosed technique. System 150 employs two stereoscopic cameras. System 150 includes a reference stereoscopic camera 152, an operational stereoscopic camera 176, 2D imaging system 154, a volumetric image detector 160 and volumetric image database 162, a registration processor 164 and a display 166. Imaging system 154 includes an imaging radiation transmitter 156 and an imaging radiation detector 158.

Registration processor 164 is coupled with reference stereoscopic camera 152, with operational stereoscopic camera 176, with imaging system 154, with volumetric image database 162 and with display 166. Volumetric image database 162 is further coupled with volumetric image detector 160.

Prior to the medical procedure, volumetric image detector 160 acquires a volumetric image (e.g., CT, MRI, PET) of the area of a spinal bone of interest such as spinal bone 168 a small and enlarged part of which depicted herein. Volumetric image detector 160 stores this volumetric image in volumetric image database 162. A representation of spinal bone 168 is apparent in the volumetric image (not shown). The volumetric image is associated with a 3D coordinate system.

During the spinal medical procedure, the user inserts a cannula 170 toward spinal bone 168. The user guides cannula 170 and needle 172 toward spinal bone 168 with the aid of images acquired by 2D imaging system 154. After the cannula 170 is inserted, the user inserts fiducial mark 176 (i.e., through cannula 170) and fixes fiducial mark 174 onto spinal bone 168. Fiducial mark 174 includes three fiducial points 172A, 172B and 172C all mounted on a single support. The user may fix fiducial mark 124 to one or both of the transverse processes or to the spinous process.

After the user fixes fiducial mark 174 onto spinal bone 168, 2D imaging system 154 acquires at least two 2D images from substantially different angles. A representation of spinal bone 168, needle 170 and a representation of fiducial mark 174 are apparent in these 2D images. The 2D images are associated with a 2D coordinate system.

During the medical procedure, an operational stereoscopic camera 176, associated with an operational stereoscopic coordinate system, may be inserted into cannula 170, and acquires an operational stereoscopic image pair of the treated area (not shown). A representation of the treated area is apparent in this operational stereoscopic image pair. When fiducial mark 174 is located in proximity to bone 168, fiducial mark 174 is also apparent in the operational stereoscopic image pair. Operational stereoscopic camera 176 may further be mounted on a surgical tool (e.g., screwdriver, surgical knife not shown). Reference stereoscopic camera 152, associated with a reference stereoscopic coordinate system, acquires a reference stereoscopic image pair (not shown). A representation of the whole surgical area and a representation of operational stereoscopic camera 176 are apparent in this reference stereoscopic image pair. When fiducial mark 174 is located distantly from bone 168 (i.e., fiducial mark 174 is not in the field of view of operational stereoscopic camera 152), then, a representation of fiducial mark 174 is apparent in the reference stereoscopic image pair. A surgical tool (not shown) may also be apparent in the reference stereoscopic image pair.

Registration processor 164 registers the reference stereoscopic coordinate system with 3D coordinate system. Registration processor 164 achieves this registration by registering the reference stereoscopic coordinate system with the 2D coordinate system and registering the 2D coordinate system with the 3D coordinate system.

Registration processor 164 registers the reference stereoscopic coordinate system with the 2D coordinate system using the representations of fiducial mark 174, apparent in the reference stereoscopic image pair and in the two 2D images. When the representation of fidudial mark 174 is apparent in the operational stereoscopic image pair, registration processor 164 registers the operational stereoscopic coordinate system with the 2D coordinate system. Registration processor 164 registers the 2D coordinate system with the 3D coordinate system using the representations of the spinal bone in the two 2D images and in the volumetric image. Registration processor further registers the reference stereoscopic coordinate system with the operational stereoscopic coordinate system (i.e., the position of the operational stereoscopic camera in the reference stereoscopic coordinate system is determined from the reference stereoscopic image pair acquired by reference stereoscopic camera 152).

Figure 3A:
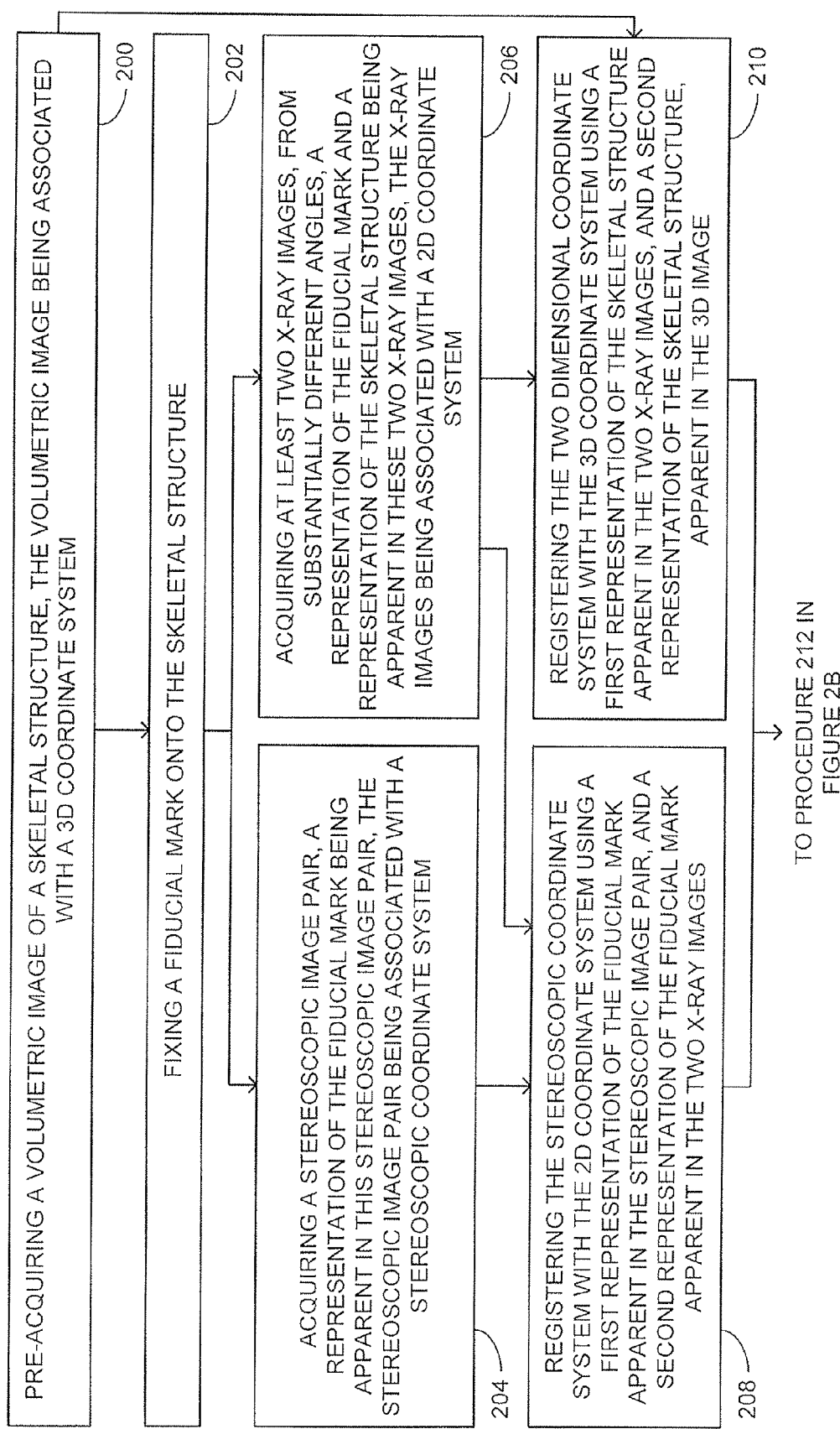
FIGS. 3A and 3B are schematic illustrations of a method for performing video based registration between images and for superimposing 3D medical information on a volumetric image, operative in accordance with a further embodiment of the disclosed technique.
Figure 3B:
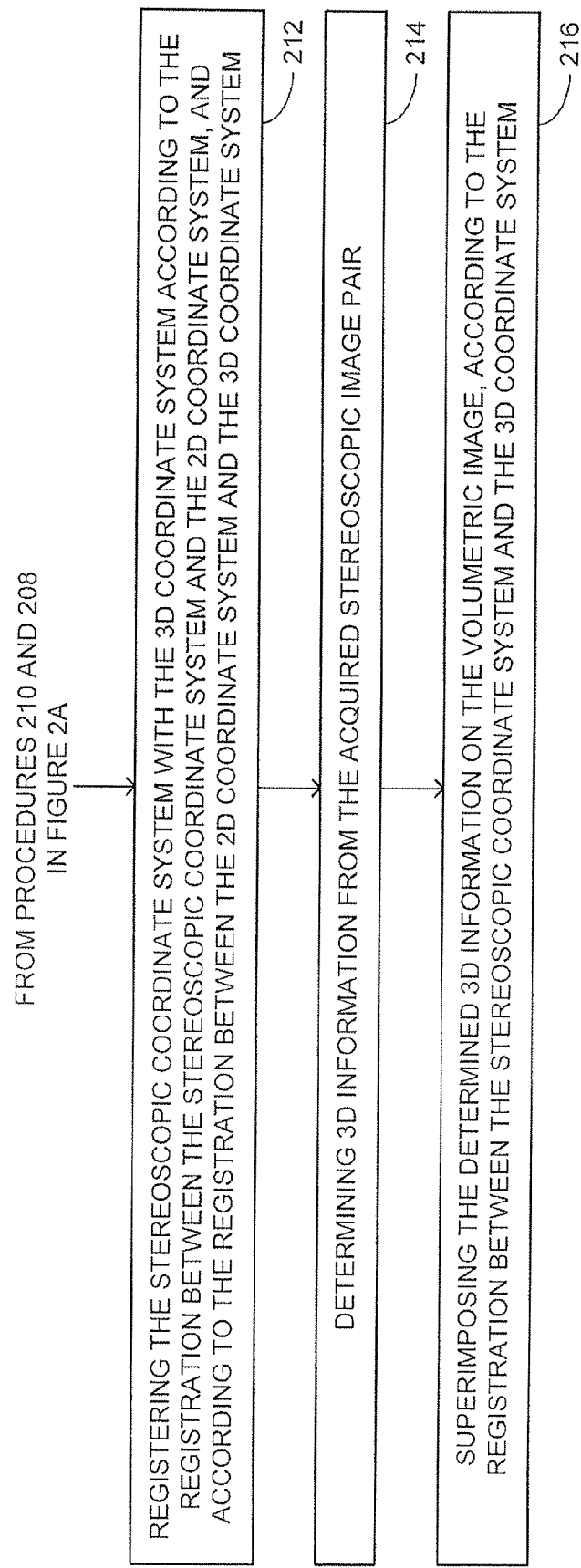

As a result of the registration, between the stereoscopic coordinate systems and the 3D coordinate system, 3D medical information, determined from the both the reference and the operational stereoscopic image pairs may be superimposed on the volumetric image. As mentioned above, this medical information may be, for example, position and orientation of a pedicle screw or of surgical tools or the coordinates of fiducial mark 174. Alternatively, registration processor 164 may superimpose 3D medical information, acquired by volumetric image detector, on the reference stereoscopic image pair or the operational stereoscopic image pair. Display 166 displays 3D medical information, determined form the distal or proximal stereoscopic image pair, superimposed on the volumetric image. Consequent to superimposing 3D medical information on the volumetric image, the user can view this 3D medical information with minimal use of fluoroscopic imaging system. It is noted that registration processor 164 registers the 3D coordinate system with the proximal stereoscopic coordinate system, and the proximal stereoscopic coordinate system with the distal stereoscopic coordinate system for each stereoscopic image pair stereoscopic camera 152 acquires (e.g., registration processor 164 adjusts the registration of the previous stereoscopic image pair for the current stereoscopic image pair Reference is now made to FIG. 3A and FIG. 3B, which are schematic illustrations of a method for performing video based registration between images and for superimposing 3D medical information on a volumetric image, operative in accordance with a further embodiment of the disclosed technique. In procedure 200 a volumetric image of a skeletal structure is acquired. This image is associated with a 3D coordinate system. The volumetric image may be stored in a database for subsequent use during a medical procedure. With reference to FIG. 1, volumetric image detector 110 acquires a volumetric image of skeletal structure and stores the acquired volumetric image in volumetric image database 112.

In procedure 202, a fiducial mark is fixed onto the skeletal structure. This fiducial mark is for example a needle fixed on to a pedicle of a vertebra. With reference to FIG. 1, fiducial 120 is fixed onto spinal bone 118.

In procedure 204, a stereoscopic image pair, is acquired. A representation of the fiducial mark is apparent on the stereoscopic image pair. The stereoscopic image pair is associated with a stereoscopic coordinate system. The stereoscopic image pair provides 3D information (e.g., the position and orientation of a pedicle screw). With reference to FIG. 1, stereoscopic camera 102 acquires a stereoscopic image pair.

In procedure 206, at least two X-ray images, from substantially different angles, are acquired. A representation of the fiducial mark and a representation of the skeletal structure are apparent in the two X-ray images. The two perpendicular x-ray images are associated with a 2D coordinate system. With reference to FIG. 1, imaging system 104 acquires two perpendicular X-ray images.

In procedure 208, the stereoscopic coordinate system is registered with the 2D coordinate system. These coordinate systems are registered using a first representation of the fiducial mark apparent in the stereoscopic image pair, and a second representation of the fiducial mark apparent in the two x-ray images. Thus, the position and orientation of the fiducial mark in both the coordinate systems is known and a transformation associating the coordinates of each point in one coordinate system to the coordinates of the same points in another coordinate system can be found. With reference to FIG. 1, registration processor 114 registers the stereoscopic coordinate system with the 2D coordinate system.

In procedure 210, the two dimensional coordinate system is registered with the 3D coordinate system using a first representation of the skeletal structure, apparent in the two x-ray images, and a second representation of the skeletal structure, apparent in the volumetric image. Thus the position and orientation of the skeletal structure in both the coordinate systems is known and a transformation associating the coordinates of each point in one coordinate system to the coordinates of the same points in another coordinate system can be found. With reference to FIG. 1, registration processor 114 registers the 2D coordinate system with the 3D coordinate system.

In procedure 212 (FIG. 3B), the stereoscopic coordinate system is the stereoscopic coordinate system registered with the 3D coordinate system according to the registration between the stereoscopic coordinate system and the 2D coordinate system and according to the registration between the 2D coordinate system and the 3D coordinate system. With reference to FIG. 1, registration processor 114 registers the stereoscopic coordinate system with the 3D coordinate system.

In procedure 214 (FIG. 3B), 3D information is determined from the acquired stereoscopic image pair. As mentioned above, this 3D information is, for example, 3D guidance information or 3D medical information. 3D guidance information is, for example, the 3D position and orientation of a medical device intended to treat a skeletal structure. 3D medical information is, for example, or size of tissues (e.g., tumors, pedicle, vertebra, spinous process, transverse process) or cavities in the treated area (e.g., resected disk, resected nucleus). With reference to FIG. 1, stereoscopic camera 102 acquires 3D medical information.

In procedure 216 (FIG. 3B), the determined 3D medical information is superimposed on the volumetric image, according to the registration between the stereoscopic coordinate system and the 3D coordinate system. Thus, for example, a representation of the position and orientation of a medical device may be superimposed on the volumetric image. The projection of the path of the medical device may further be projected on the volumetric image. As a further example, size of tissues (e.g., tumors) or cavities may also be super-imposed on the volumetric image. With reference to FIG. 1, registration processor 114 superimposes the stereoscopic image pair on the volumetric image. Display 116 displays the superimposed image.

Figure 4:
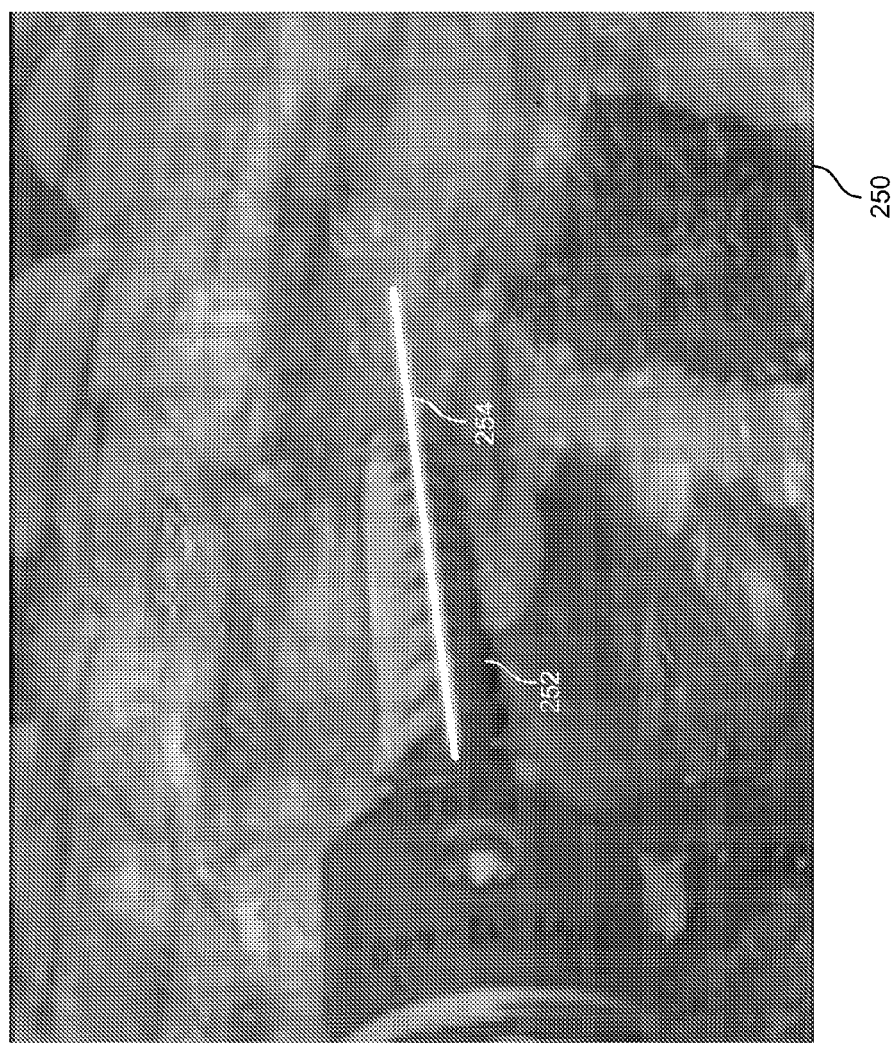
FIG. 4 is a schematic illustration of 3D medical image superimposed with a representation of a medical device and with a projection of the path of the medical device, in accordance with another embodiment of the disclosed technique.

Reference is now made to FIG. 4, which is a schematic illustration of 3D medical image 250 superimposed with a representation of a medical device and with a projection of the path of the medical device, in accordance with another embodiment of the disclosed technique. In 3D medical image 250, a representation 252 is the representation of a pedicle screw and projection 254 represents the projected path of the pedicle screw.

Figure 5:
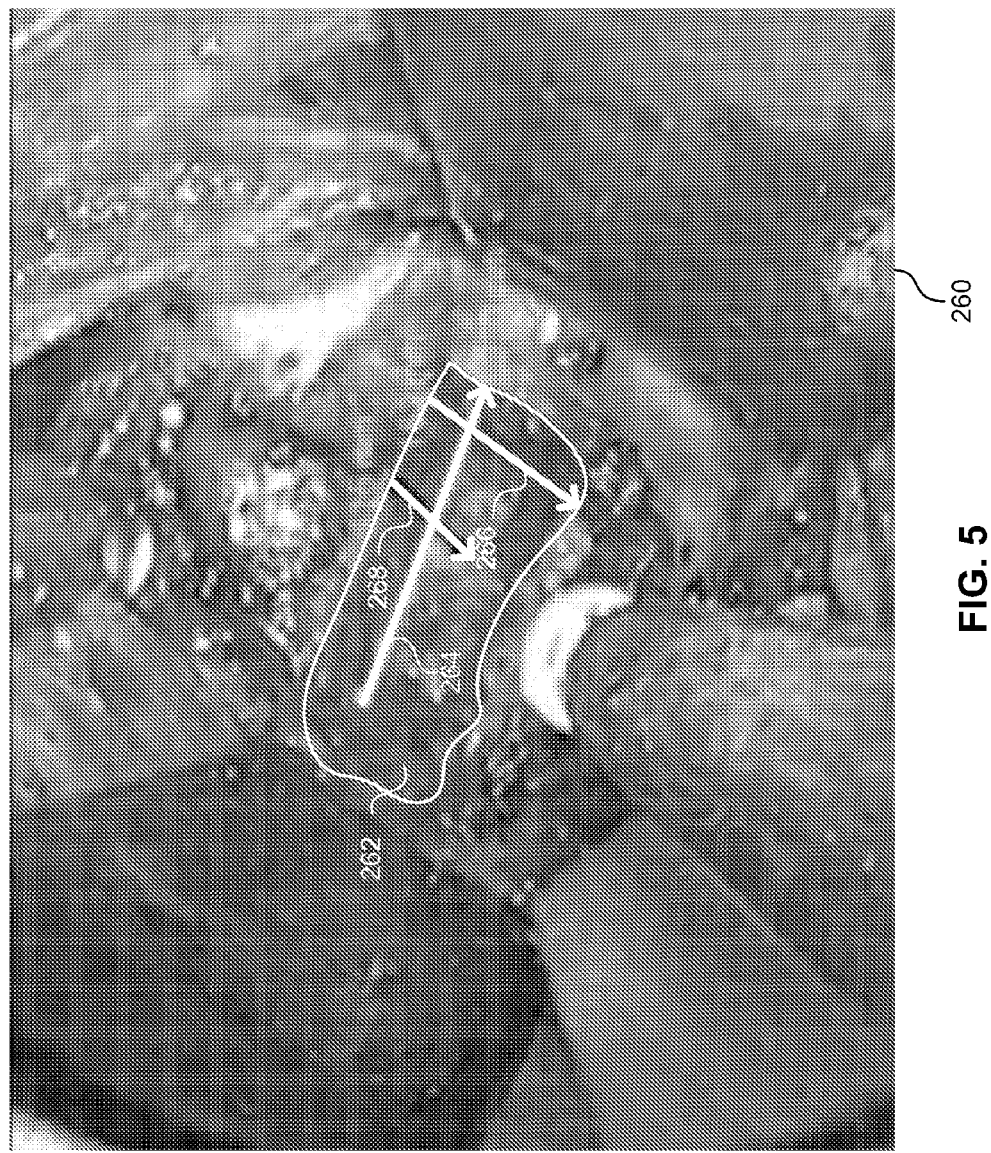
FIG. 5 is a schematic illustration of an image with a representation of the dimensions of a cavity, in accordance with a further embodiment of the disclosed technique.

Reference is now made to FIG. 5, which is a schematic illustration of an image 260 with a representation of the dimensions of a cavity 262, in accordance with a further embodiment of the disclosed technique. In medical image 260, arrow 264 represents the length of the cavity, arrow 266 represents the width of the cavity and arrow 268 represents the depth of the cavity. These cavity dimensions may be superimposed on a volumetric image. Thus, the user can determined the desired size of an implant intended to be implanted into the cavity.

Figure 6:
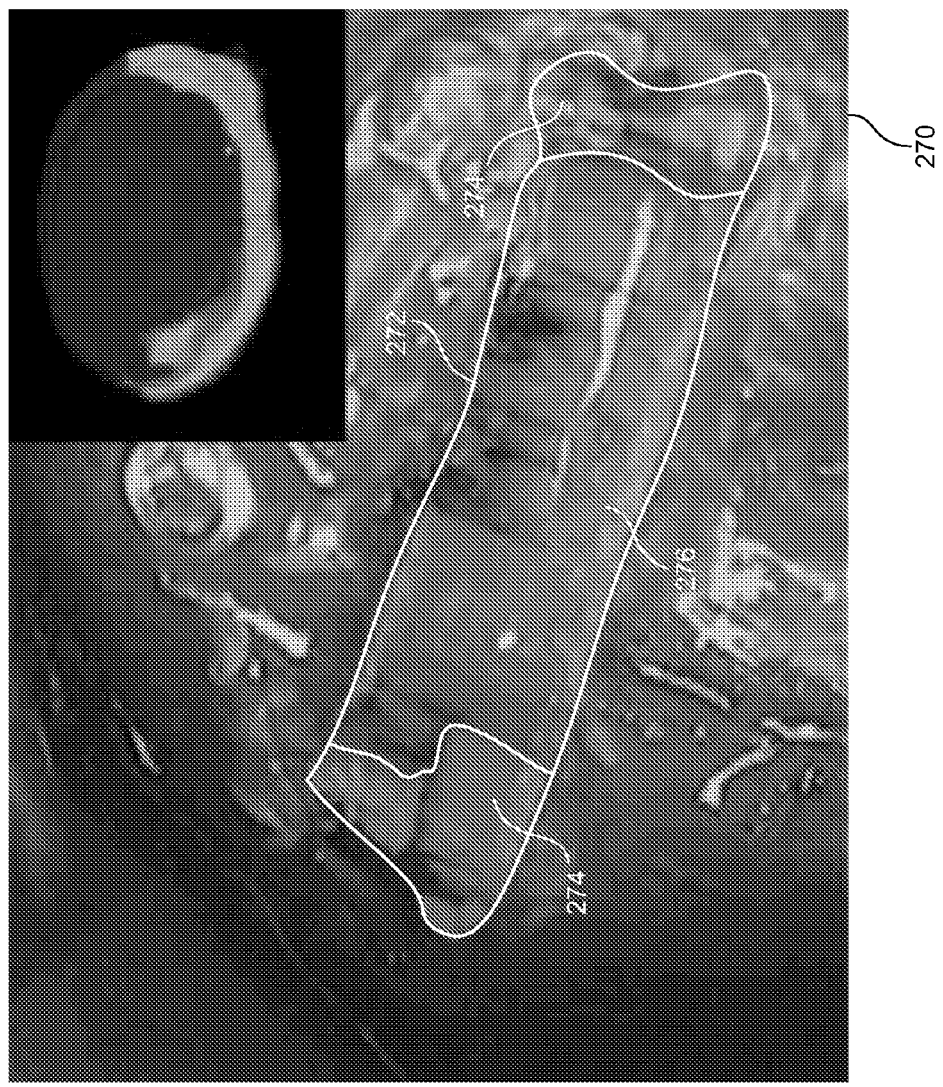
FIG. 6 is a schematic illustration of an image with a representation of a partially resected disc, in accordance with another embodiment of the disclosed technique.

Reference is now made to FIG. 6, which is a schematic illustration of an image 270 with a representation of a partially resected disc 272, in accordance with another embodiment of the disclosed technique. The partially resected part of the disc, reference 274, and the remaining part of the disc, reference 276, may be superimposed on a volumetric image.

During the medical procedure the patient may move. Consequent to this movement, stereoscopic coordinate system and the 3D coordinate system may no longer be registered. Referring back to FIG. 1, additional fiducials (not shown) are fixed on canulla 120. Thus, camera 102 can detect the movement of the patient or of the cannula. Registration processor 114 reregisters the stereoscopic coordinate system with the 3D coordinate system according to the detected movement.

Figure 7B:
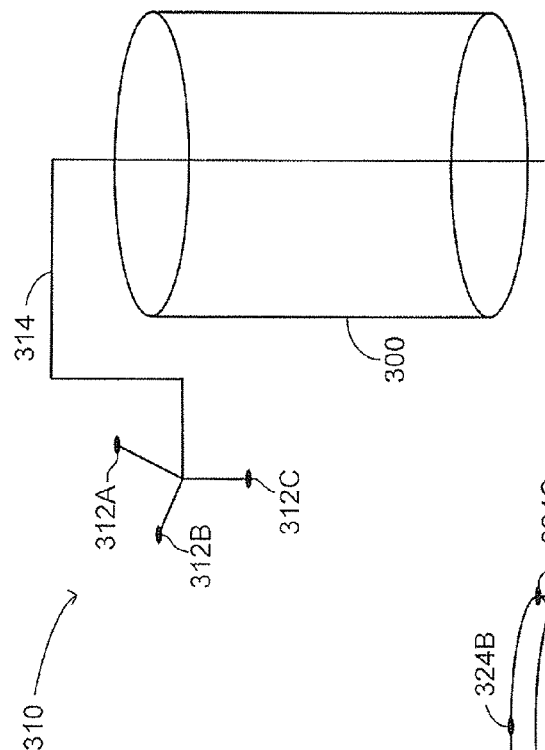
FIGS. 7A and 7B are schematic illustrations of different fiducial marks in accordance with a further embodiment of the disclosed technique.
Figure 7A:
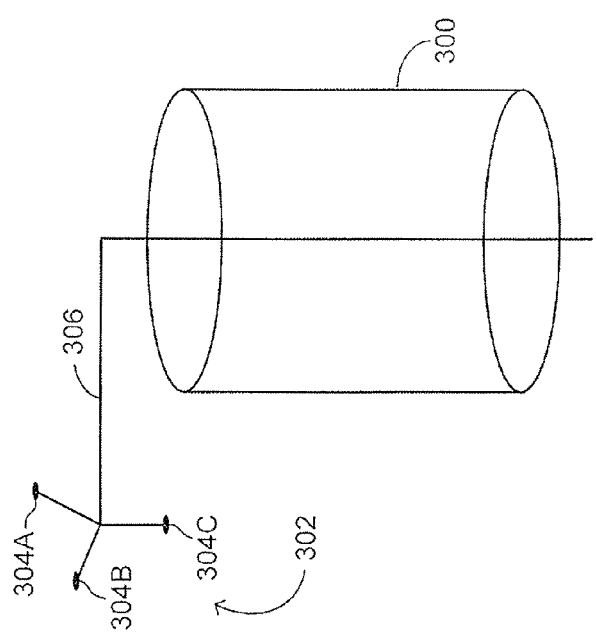

As mentioned above, a fiducial mark is fixed onto the skeletal or joint structure (e.g., to one of the transverse processes of a vertebra during a spinal surgery procedure). However, it is required that the fiducial mark shall not disturb the surgical tools. In general, fiducial marks have at least three fiducial points to allow 3D registration. Reference is now made to FIG. 7A and FIG. 7B, which are schematic illustrations of different fiducial marks, generally referenced 302 and 310 respectively, in accordance with a further embodiment of the disclosed technique. In FIGS. 7A, fiducial mark 302 has three fiducial points 304A, 304B and 304C. Fiducial mark 302 is located outside cannula 300. Fiducial mark 302 is fixed to a bone (e.g., to the transverse process of a vertebra, not shown) by support 306. In FIG. 7B fiducial mark 310 has three fiducial points 312A, 312B and 312C. Fiducial mark 310 is located outside cannula 300. Fiducial mark 302 is fixed to a bone (e.g., to the transverse process of a vertebra, not shown) by support 314, which is bent toward cannula 300 to decrease the interference of fiducial mark 310 with surgical instrumentation (not shown).

Figure 8:
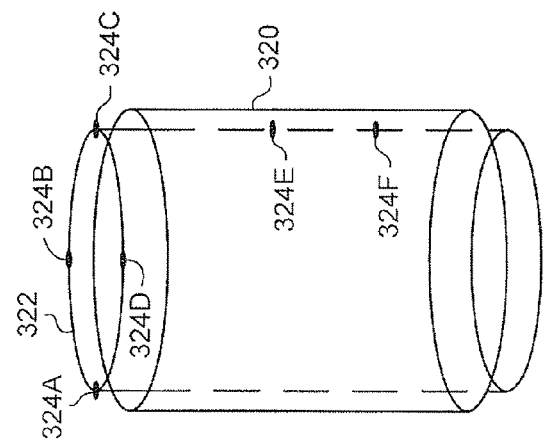
FIG. 8 is a schematic illustration of a fiducial mark in accordance with another embodiment of the disclosed technique.

Reference is now made to FIG. 8, which is a schematic illustration of a fiducial mark generally reference 322 in accordance with another embodiment of the disclosed technique. Fiducial mark 322 is in the form of a tube inserted into cannula 320. Fiducial mark 322 includes fiducial points 324A, 324B, 324C and 324D located on the upper rim of fiducial mark 322. Fiducial mark 322 further includes fiducial points 324E and 324F located within fiducial mark 322. Fiducial mark 322 is fixed onto a bone (e.g., a spinous process of a vertebra not shown). Consequently, with reference to FIG. 1, registration processor 114 can register the 3D or 2D coordinate systems with the stereoscopic coordinate system even when stereoscopic camera 102 is inserted into cannula 120.

Figure 9C:
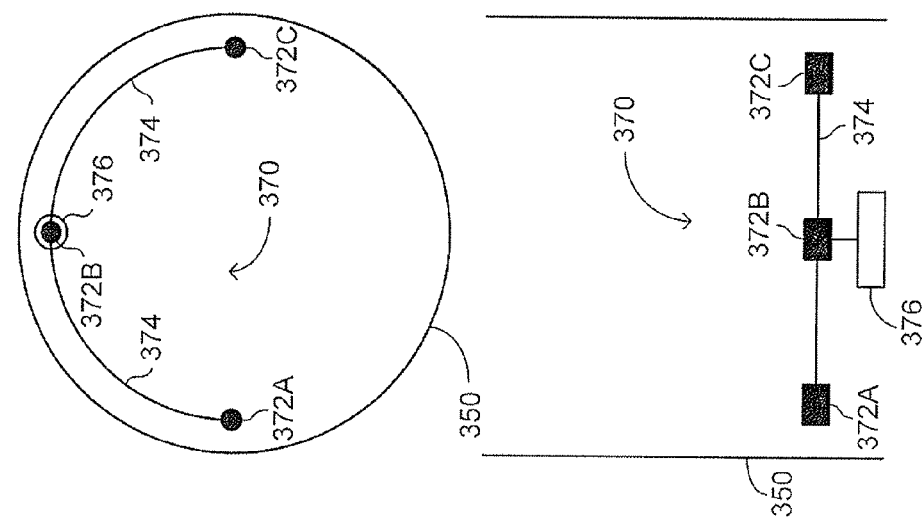
FIGS. 9A, 9B, 9C, 9D and 9E are schematic illustrations of fiducial marks in accordance with a further embodiment of the disclosed technique.
Figure 9B:
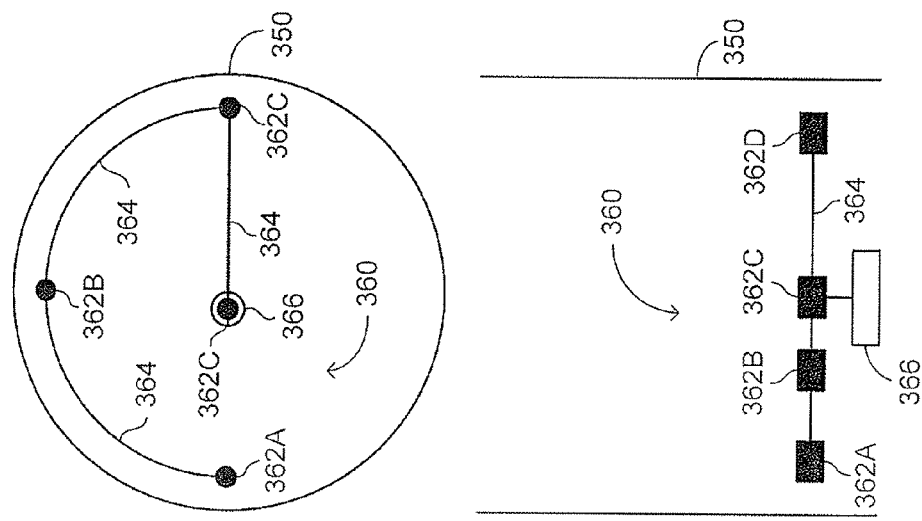
Figure 9A:
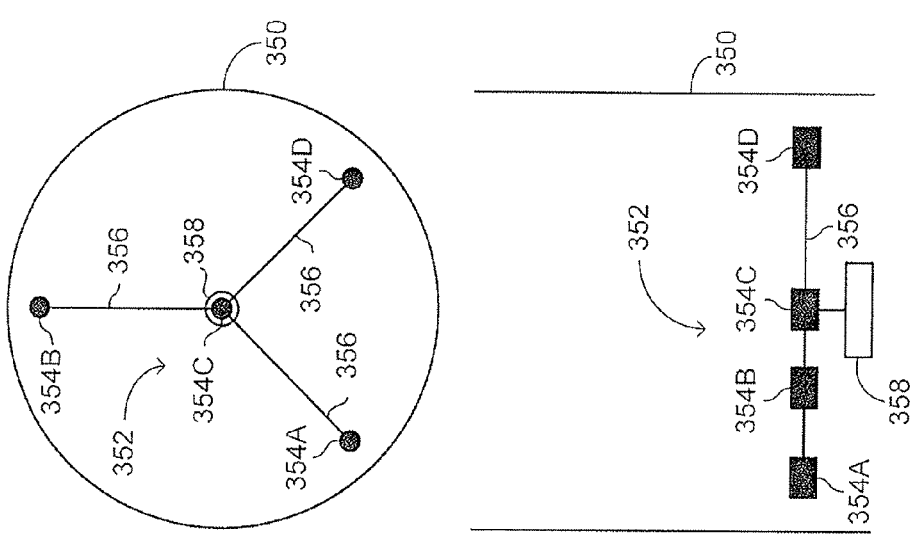

Reference is now made to FIGS. 9A, 9B, 9C, 9D and 9E which are schematic illustrations of fiducial marks 352, 360, 370, 380 and 390 respectively, in accordance with a further embodiment of the disclosed technique. In FIG. 9A, fiducial mark 352 includes four fiducial points 354A, 354B, 354C and 354D which are mounted on support 356. Support 356 has the shape of three rods connected at a single point on the longitudinal axis of cannula 350. Support 356 is fixed to a bone (not shown) with screw 358 connected to support 356. In FIG. 9B, fiducial mark 360 includes four fiducial points 362A, 362B, 362C and 362D which are mounted on support 364. Support 364 has the shape of an arc to which at one end thereof, one end of a rod is connected. The other end of the rod is located at a point on the longitudinal axis of cannula 340. Support 364 is fixed to the bone (not shown) with screw 366 connected to support 364.

In FIG. 9C, fiducial mark 370 includes three fiducial points 372A, 372B and 372C which are mounted on support 374. Support 374 has the shape of an arc. Support 374 and thus fiducial mark 370 is fixed to a bone (not shown) with screw 376 connected to support 374. Screw 376 is located off the longitudinal axis of cannula 350 and toward the circumference of cannula 350.

Figure 9E:
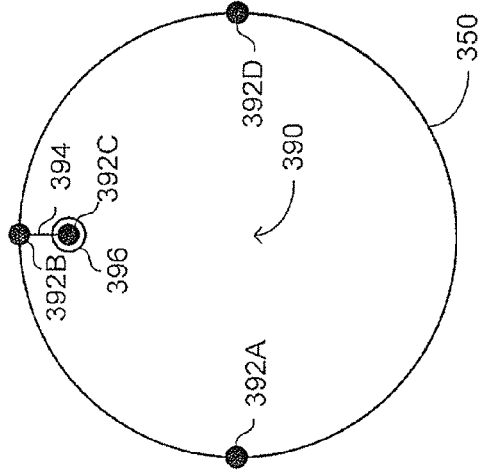
Figure 9E:
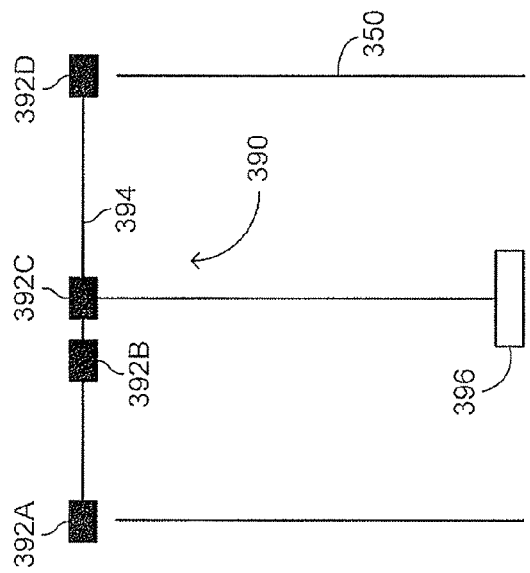
Figure 9D:
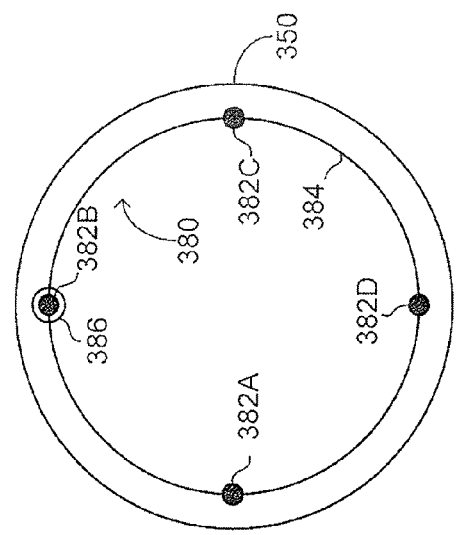
Figure 9D:
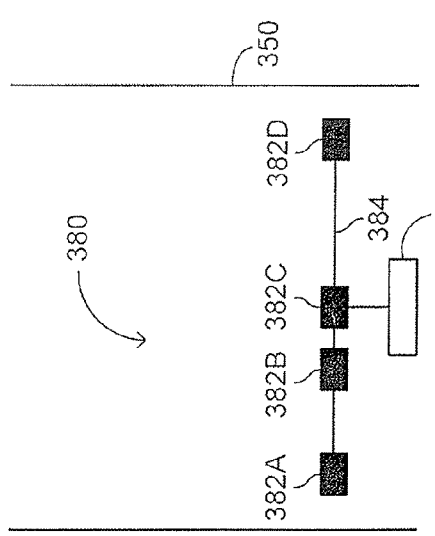

In FIG. 9D, fiducial mark 380 includes four fiducial points 382A, 382B, 382C which are mounted on support 384. Support 384 has the shape of a ring. Support 384 and thus fiducial mark 380 is fixed to a bone (not shown) with screw 386 connected to support 384. Screw 386 is located off the longitudinal axis of cannula 350 and toward the circumference of cannula 350.

In FIGS. 9A, 9B, 9C and 9D, fiducial marks 352, 360, 370 and 380 are located at the bottom of cannula 350. Thus, the interference of fiducial marks 352, 360, 370 and 380 with the surgical instrumentation (not shown) is reduced.

In FIG. 9E, fiducial mark 390 includes four fiducial points 392A, 392B, 392C which are mounted on support 394. Support 394 has the shape of a ring with a stub extending toward the longitudinal axis of cannula 350. Support 394 is located above the upper rim of cannula 350, thus Fiducial mark 390 does not interfere with surgical instrumentation (not shown) inserted into cannula 350. Support 394 and thus fiducial mark 390 is fixed to a bone (not shown) with screw 396 connected to the stub. Screw 396 is located off the longitudinal axis of cannula 350 and toward the circumference thereof.

It will be appreciated by persons skilled in the art that the disclosed technique is not limited to what has been particularly shown and described hereinabove. Rather the scope of the disclosed technique is defined only by the claims, which follow.

The invention claimed is:

1. A system for video based registration between images during a skeletal medical procedure, said system comprising:
    a stereoscopic camera, associated with a stereoscopic coordinate system, for acquiring a stereoscopic image pair of a fiducial mark said fiducial mark being fixed onto a skeletal structure, a first fiducial representation of said fiducial mark being apparent on said stereoscopic image pair;
    a two dimensional (2D) image detector, associated with a 2D coordinate system, for acquiring at least two substantially different images of said skeletal structure, a second fiducial representation of said fiducial mark and a first skeletal representation of said skeletal structure being apparent on said two substantially different 2D images; and
    a registration processor, coupled with said stereoscopic camera and with said 2D image detector, registering said stereoscopic coordinate system with a three dimensional (3D) coordinate system associated with a volumetric image detector, and for superimposing 3D information on at least one volumetric image, acquired by said volumetric image detector, according to said registration, said at least one volumetric image being devoid of said fiducial mark, said registration processor registering said stereoscopic coordinate system with said 3D coordinate system by registering said stereoscopic coordinate system with said 2D coordinate system using said first fiducial representation apparent in said stereoscopic image pair, and said second fiducial representation apparent in said two substantially different 2D images, and by registering said 2D coordinate system with said 3D coordinate system using said first skeletal representation apparent in said two substantially different 2D images, and said second skeletal representation apparent in said at least one volumetric image; and a display displaying a registered image stereoscopically, said registered image comprising said stereoscopic image pair in said stereoscopic coordinate system and said volumetric image in said 3D coordinate system.

2. The system according to claim 1, further including a volumetric image database, coupled with said registration processor, providing said at least one volumetric image to said registration processor.

3. The system according to claim 2, further including said volumetric image detector coupled with said volumetric image database, providing said at least one image to said volumetric image database.

4. The system according to claim 1, further including said volumetric image detector coupled with said registration processor, providing said at least one image to said registration processor.

5. The system according to claim 1, further including another stereoscopic camera coupled with said registration processor, for acquiring another stereoscopic image pair, said stereoscopic camera being apparent on said other stereoscopic image pair.

6. The system according to claim 1, wherein said stereoscopic camera is fitted onto a medical device.

7. The system according to claim 6, wherein said medical device is selected from said group consisting of:
 a pedicle screw;
 a rod; and
 a joint.

8. The system according to claim 1, wherein said stereoscopic camera is fitted onto a surgical tool.

9. The system according to claim 8, wherein said surgical tool is selected from said group consisting of:
 a screwdriver;
 a drill; and
 a surgical knife.

10. The system according to claim 1, wherein said registration processor superimposes 3D information, determined from said stereoscopic image pair, on said volumetric image.

11. The system according to claim 10, wherein said 3D information is 3D medical information and 3D guidance information.

12. The system according to claim 1, further comprising a display, coupled with said registration processor, said display displaying said stereoscopic image pair.

13. The system according to claim 12, wherein said display displays said volumetric image superimposed on said stereoscopic image pair.

14. The system according to claim 1, wherein said fiducial mark, being introduced into a cannula, comprises:
 a tube, a first group of fiducial points and a second group of fiducial points, said tube includes screws for attaching said tube onto said skeletal structure, said first group of fiducial points being located on the rim of said tube, said second group of fiducial point being located within said tube, said tube having a diameter smaller than said cannula.

15. The system according to claim 1, wherein said fiducial mark, being introduced into a cannula, comprises:
 a plurality of fiducial points, a plurality of rods and a screw for attaching said fiducial mark to said skeletal structure, one end of each of said rods, all being coupled to each other at a single point, each one of said fiducial marks being coupled at each of said other ends of said rods, said screw being coupled to said rods at said point.

16. The system according to claim 15, wherein said point is located on said longitudinal axis of said cannula.

17. The system according to claim 1, wherein said fiducial mark, being introduced into a cannula, comprises:
 a plurality of fiducial points, an arc, a rod and a screw for attaching said fiducial mark to said skeletal structure, one end of said rod is coupled with one and of said arc, said screw is coupled with the other end of said rod, said fiducial points being located along said arc.

18. The system according to claim 17, wherein said other end of said rod is located at said longitudinal axis of said cannula.

19. The system according to claim 1, wherein said fiducial mark, being introduced into a cannula, comprises:
 a plurality of fiducial points, an arc and a screw for attaching said fiducial mark to said skeletal structure, said screw is coupled with said arc, said fiducial points being located along said arc.

20. The system according to claim 1, wherein said fiducial mark, being introduced into a cannula, comprises:
 a plurality of fiducial points, a ring and a screw for attaching said fiducial mark to said skeletal structure, said screw is coupled with said ring, said fiducial points being located along said ring.

21. The system according to claim 1, wherein said fiducial mark, being introduced into a cannula, comprises:
 a plurality of fiducial points, a ring and a screw for attaching said fiducial mark to said skeletal structure, said ring having a diameter at least equal to said diameter of said cannula, said screw is coupled with said ring and being located within said cannula, said fiducial points being located along said ring.

22. A method for video based registration between images during a skeletal medical procedure, said method comprising said procedures of:
 pre-acquiring a volumetric image of said skeletal structure, said at least one volumetric image being associated with a three dimensional (3D) coordinate system;
 fixing a fiducial mark onto said skeletal structure after said procedure of pre-acquiring is complete, said volumetric image being devoid of said fiducial mark;
 acquiring a stereoscopic image pair, said stereoscopic image pair, a first fiducial representation of said fiducial mark being apparent on said stereoscopic image pair, said stereoscopic image pair being associated with a stereoscopic coordinate system;
 acquiring at least two substantially different two dimensional (2D) images, a second fiducial representation of said fiducial mark, and a first skeletal representation of said skeletal structure, both being apparent on said at least two substantially different 2D images, said at least two substantially different 2D images being associated with a 2D coordinate system;

registering said stereoscopic coordinate system with said 2D coordinate system using said first fiducial representation apparent in said stereoscopic image pair, and said second fiducial representation apparent in said at least two substantially different 2D images;

registering said 2D coordinate system with said 3D coordinate system using said first skeletal representation apparent in said at least two substantially different 2D images, and a second skeletal representation of said skeletal structure, said second skeletal representation being included in said at least one volumetric image;

registering said stereoscopic coordinate system with said 3D coordinate system, according to said registrations between said stereoscopic coordinate system and said 2D coordinate system and according to said registration between said 2D coordinate system and said 3D coordinate system; and displaying a registered image stereoscopically, said registered image comprising said stereoscopic image pair in said stereoscopic coordinate system and said volumetric image in said 3D coordinate system.

23. The method according to claim 22 further comprising said procedures of:
  determining 3D information from said acquired stereoscopic image pair; and
  superimposing said 3D information on said volumetric image according to said registration between said stereoscopic coordinate system and said 3D coordinate system.

24. The method according to claim 23, wherein said 3D information 3D medical information and 3D guidance information.

25. The method according to claim 22 further comprising said procedure of superimposing said volumetric image on said stereoscopic image pair, according to said registration between said stereoscopic coordinate system and said 3D coordinate system.

* * * * *